US005322648A

United States Patent [19]

Dapper

[11] Patent Number: 5,322,648
[45] Date of Patent: Jun. 21, 1994

[54] PROCESS FOR FORMING SHAPED COLLAGEN DEVICES

[75] Inventor: Gregory S. Dapper, Newark, Calif.

[73] Assignee: Vitaphore Corporation, Menlo Park, Calif.

[21] Appl. No.: 750,079

[22] Filed: Aug. 26, 1991

[51] Int. Cl.$^5$ ............................................... B29D 11/00
[52] U.S. Cl. ........................................ 264/1.1; 264/1.4;
264/2.5; 264/22; 264/330; 1/331.22
[58] Field of Search ............... 264/2.6, 330, 331.22, 264/1.1, 1.4, 22

[56] References Cited

U.S. PATENT DOCUMENTS

| | | | |
|---|---|---|---|
| 4,164,559 | 8/1979 | Miyata | 424/14 |
| 4,260,228 | 4/1981 | Miyata | 351/160 H |
| 4,268,131 | 5/1981 | Miyata | 351/160 H |
| 4,273,734 | 6/1981 | Siderman | 264/1.1 |
| 4,365,050 | 12/1982 | Ivani | 527/312 |
| 4,408,845 | 10/1983 | Siderman | 351/160 H |
| 4,447,562 | 5/1984 | Ivani | 523/105 |
| 4,650,616 | 3/1987 | Wajo | 264/2.6 |
| 4,655,980 | 4/1987 | Chu | 264/202 |
| 4,687,518 | 8/1987 | Miyata | 106/161 |
| 4,713,375 | 12/1987 | Lindstrom | 514/57 |
| 4,793,344 | 12/1988 | Cumming | 128/305 |
| 4,879,072 | 11/1989 | Bourset | 264/1.4 |
| 4,913,904 | 4/1990 | Fyodorov | 424/427 |
| 4,946,450 | 8/1990 | Erwin | 604/294 |
| 4,948,540 | 8/1990 | Nigam | 264/320 |

Primary Examiner—James Lowe
Attorney, Agent, or Firm—Reginald J. Suyat

[57] ABSTRACT

A method is provided for fabricating a shaped article from aqueous collagen-containing materials. A dispersion containing collagen and a surfactant is cast upon a mold of thermoplastic material and dried by a ramped drying profile under controlled conditions of relative humidity and temperature. The controlled drying allows for initial renaturation of the collagen dispersion then drying at high humidity to form a product with minimal residual stress.

20 Claims, No Drawings

PROCESS FOR FORMING SHAPED COLLAGEN DEVICES

FIELD OF THE INVENTION

The present invention is directed to a method for fabricating a shaped article from aqueous collagen-containing materials. In particular, the present invention is directed to a method for forming ophthalmic devices characterized by low residual stress.

BACKGROUND OF THE INVENTION

The present invention is directed to solving a problem which occurs during the manufacture of shaped devices formed from aqueous collagen-containing dispersions. The present invention is particularly useful for forming shaped ophthalmic devices which retain a predetermined curvature. It is therefore imperative that there not be a memory imposed on the device during the manufacturing process which would distort the device into a configuration other than the predetermined desired shape. Although the process of the present invention is applicable to any shaped collagen-containing device, it is particularly useful for the formation of lenticular devices used for ophthalmologic treatment of trauma, post-surgical care, and for delivery of therapeutic agents to the eye. Such devices, in the shape of a thin lens, are usually biodegradable, hydrophilic and lubricous.

The material most commonly used for fabricating such devices is a high-purity collagen protein, such as those available from bovine corium or tendon.

Commonly used methods for producing such devices include film-forming methods, such as the casting of a collagen dispersion over a mold of a predetermined desired shape. A major problem in the production of such devices by these methods is the creation of residual stresses during drying which result in deformation from the cast shape upon rehydration of the device. Such deformation in the instance of a lenticular shape is usually manifested by a flattening or cone shape as opposed to the desired curved shape. The deformation can cause various problems during usage of the device on the eye, such as difficulty in placement, poor retention and discomfort.

Another major problem in manufacturing collagen-containing devices is associated with the drying period. Lenticular devices such as those described above may be dried over a period of several days using heat (at a relatively constant temperature) and high humidity. Under such conditions, microbial growth is a problem, leading to unacceptable products. It is desirable therefore to provide a method for drying collagen devices rapidly to minimize or eliminate microbial and endotoxin contamination.

It is therefore an object of the present invention to provide a method for rapidly drying devices formed from aqueous collagen-containing dispersions to minimize or to avoid microbial growth and endotoxin production.

It is another object of the present invention to provide a process for controlling the residual stresses in a casting operation to form films from aqueous collagen-containing dispersions.

It is yet another object of the present invention to provide a residual stress-free collagen ophthalmic device.

These objects and other objects may be provided by the following description and by practice of the invention.

SUMMARY OF THE INVENTION

A method is provided for fabricating a shaped article from aqueous collagen-containing materials whereby the article is made with minimal, if any, deformation due to residual stress from a predetermined shape defined by the mold upon which the article is formed by casting. The method comprises the steps of casting an aqueous collagen-containing material upon the mold; partially drying the material at a temperature less than the temperature at which collagen denaturation occurs for a period of time sufficient to set the form upon the mold; continuing the drying in a relative humidity in the range of 80–99% at a temperature less than the temperature at which collagen denaturation occurs for a period sufficient to provide the shaped article in solid form with minimal residual stress. Once the device is formed with minimal residual stress in this manner stresses can no longer be introduced, so the drying may be completed at higher temperatures, i.e., up to about 27° C., at a relative humidity in the range of about 90–99%.

A preferred embodiment comprises the steps of casting the aqueous collagen-containing material on a mold; partially drying the material for a period up to about four hours within a temperature range of about 17° to 19° C. in an atmosphere of relative humidity within the range of about 50% to 65%; continuing the drying for an additional period of up to about three hours within a temperature range of about 17° to 19° C. in an atmosphere of relative humidity within the range of about 85% to 95%; and completing the drying process within the temperature of about 22° to 27° C. in an atmosphere of relative humidity within the range of about 90% to 95%. In a preferred embodiment, the mold which is utilized for the casting and drying procedure to impart the desired shape to the collagen device has a thermoplastic contacting surface, such as polycarbonate, polyalkylene or polyurethane. Preferably, the aqueous dispersion containing the collagen should also contain a surface-active material such as hydroxyethyl cellulose, polyethylene glycol, glycerin, polyvinyl alcohol, polyvinyl pyrollidone, polyethylene polypropylene glycols, polysorbates, and the like.

DESCRIPTION OF THE PREFERRED EMBODIMENTS

The aqueous collagen-containing dispersion used as a starting material for the present process may be formed from any type of collagen which is suitable for the end use of the shaped article. The preferred collagen is a purified collagen derived from bovine corium or tendon, however, other types of collagen may be utilized, such as animal sclera or placenta. It will be realized that other types of collagen may also be acceptable, depending upon the intended end use of the shaped product. In a preferred embodiment according to the present invention for ophthalmological uses, native collagen derived from animal skins and tendons may have antigenic properties and therefore are to be avoided. However, for other end uses such collagens may be useful. The preferred collagen for the ophthalmological uses are those prepared by methods known in the art such as enzyme solubilized collagen and chemically solubilized collagen.

The collagen-containing dispersions should have a physiologic pH, that is, a pH in the relatively narrow range of pH normally encountered in the fluids of the human body, generally in the range of about 6.5 to about 8.0. The concentration of the collagen in the dispersions will depend upon the particular processing viscosity and end product thickness which is desired.

Chemical modification of the collagen, such as modification of the amino groups or carboxyl groups by acylation or esterification, is in general not desired since it may increase the possibility of adverse reactions to the user. However, such chemically modified collagen may in some instances be useful and therefore are not excluded from the scope of the present invention.

In the most preferred embodiment of the present invention the dispersion will also contain surfactant materials which will assist in the release of the dried device from the mold, provide for even distribution of the film and also provide for the desired product thickness profile on the mold with minimal formation of imperfections. Such surfactants include, but are not limited to, biologically acceptable materials such as hydroxyethyl cellulose, polyethylene glycol, glycerine, polyvinyl alcohol, and polyvinyl pyrrolidones, polyethylene polypropylene glycols and polysorbates such as Triton ® and Pluronic ® (BASF). The amount of the surfactant utilized in the dispersion which has been generally found to be useful is from 0.001 to 1% (wt/volume). It will be realized that the maximum amount of surfactant which may be utilized will be limited by adverse affects which may be created on the structural integrity of the final molded product or any adverse affect on other desired properties of the final product such as toxicity or drug release rate, if a drug is also incorporated into the final product. The minimum amount of the surfactant to be utilized is that required to provide smooth release of the dried product from the mold without distortion or deformation or creation of other undesirable optical or physical defects in the final product.

Other solids besides the collagen and surfactant may be included in the dispersion, if desired, provided that these solids are biologically acceptable and provided that the total solids concentration in the dispersion is sufficient to cast a film upon the mold of the desired consistency. Such additional materials may include drugs, such as antibiotics, steroids or drug release-enhancing agents.

For ophthalmologic devices, the preferred solids concentration over the dispersion which is useful is in the range of about 0.5 to 3.0 wt %.

The pH of the dispersion is preferably a physiologic pH as described above, which is attainable by using collagen and neutral surfactants in the dispersion. In some instances, depending upon the source of collagen and the processing used to produce the collagen, the dispersion may initially have a pH outside of the physiologic pH in which case the pH may be adjusted by using sodium or potassium hydroxides and phosphates, hydrochloric and phosphoric acid or any other biologically acceptable buffering agent.

The preferred surfactants are hydroxyethyl cellulose and polyethylene polypropylene glycols (a species of which is sold under the trade name Pluronic).

The casting molds used to form the collagen materials according to the present invention are preferably thermoplastic materials such as polycarbonate, polyethylene, polypropylene, polyurethane, etc. The particularly preferred mold materials are polycarbonate and polypropylene which have advantageous surface wetting properties of inducing minimal residual stress on the device or providing facile release characteristics of the device from the mold.

We have found, surprisingly, that a ramped drying profile of the cast dispersion under controlled relative humidity provides products characterized by minimal residual stress thereby reducing or eliminating residual stress related deformation, while minimizing drying time.

The first step in the drying procedure is conducted at a temperature less than the temperature at which collagen denaturation occurs for a period of time sufficient to set the form of the device upon the mold. This first step is believed to be important in minimizing the drying time of the overall process. The relative humidity during this step is not particularly critical but it is preferred to be lower than about 80% and preferrably about 50–65%. This step is conducted for a period of time to allow the collagen to at least partially renaturize which assists in allowing the device to set upon the mold. This typically will occur during a period of less than about four hours when drying a thin film of collagen-containing material.

The second step is generally useful for minimizing the residual stress, therefore it is important the humidity be higher, usually about 80–99% relative humidity. The temperature should still be maintained lower than the temperature at which collagen is denaturized. For a thin film of collagen-containing material, this step of the drying period is usually less than about three hours. After completion of the second step, usually all that remains is to complete the drying at a higher temperature, usually about 22°–27° C. at a high relative humidity, usually 80–99%, and preferably above 85%, until the device is completely dry or is as dry as desired.

For drying collagen-containing dispersions cast as films, a preferred drying profile comprises a threestep ramp described as follows. To minimize drying time, the cast materials are first dried for a period of up to about four hours within a temperature range of 17° to 19° C. at a relative humidity within the range of 50% to 65%. To minimize residual stress, the humidity is then increased to about 85% to 95% and drying is continued for an additional period of up to about three hours within a temperature range of 17° to 19° C. Finally, the drying is completed within the temperature range of about 22° to 27° C. at a relative humidity within the range of about 90% to 95%.

While not intending to be bound by any particular theory, it is believed that the first step of the drying process at 50% to 65% relative humidity promotes partial renaturation of the collagen dispersion. The next step at about 85% to 95% relative humidity is believed to maintain the low temperature of the first step while increasing the humidity toward the value which is useful for the reduction of residual stress during drying. The final step at 22° to 27° C. is held until the device is completely dry.

The process of drying according to the present invention surprisingly results in not only minimizing the residual stress in the end product, but also minimizes the drying time which is important to minimize or eliminate contamination by bacterial growth and by the endotoxins produced by many bacteria. In general, the shorter the drying time, the less the likelihood of bacterial growth and thus endotoxin production.

Useful drying times for ophthalmic devices are between about 20 and 24 hours but may differ for other types of applications.

Subsequent to drying it is preferred that the shaped article be crosslinked to protect against bioerodibility. Conventional dry crosslinking methods may be utilized such as by dehydrothermal methods at high temperature and low pressure or by UV radiation.

The process according to the present invention is useful for preparing collagen materials into various shapes from aqueous collagen dispersions wherein the final shape must closely follow the fabricated shape with minimal deformation during usage. Other devices include shaped wound dressings, tissue adhesion barriers and percutaneous coverings. The present invention is particularly advantageous for ophthalmic collagen coverings which have essentially a spherical shape repeating the curvature of the front section of the eye and ensuring full contact with the surface of the cornea. Such ophthalmic collagen coverings may be applied to the front surface of the cornea and serve as a temporary hydrophilic spherical bandage and be retained upon the cornea without any additional fixation.

Having described the preferred embodiment of the invention, the following examples are provided by way of illustration but are not intended to limit the invention in any way.

EXAMPLE 1—Fabrication of ophthalmic bandage device

A sample of 3.5 grams of chemically treated bovine corium collagen is centrifuged in 800 ml of RO water for 30 minutes at 4000 RPM to remove residual salts. The resultant collagen is then solubilized making a dispersion with a final solids concentration of 2% and a final pH of 8 (pH adjusted with potassium hydroxide). To the collagen dispersion is added Poloxamer 331 to achieve a concentration of 0.003%. The dispersion is then cast into concave semi spherically shaped polypropylene molds. The cast dispersion is dried in a two step process in a humidity/temperature controlled chamber. The first step involves a 5 hour step at 18.5 C and 65% RH, and the second step involves a cycle at 25 C and 93% RH until the shields are dry. The dried collagen shield is then dehydrothermally crosslinked at 125 C and $10^{-2}$ Torr. The crosslinked product is clear, piable, and has a semi-spherical shape which conforms to the curvature of the eye.

EXAMPLE 2—Fabrication of ophthalmic bandage device

A sample of 3.5 grams of chemically treated bovine corium collagen is centrifuged in 800 ml of RO water for 30 minutes at 4000 RPM to remove residual salts. The resultant collagen is then solubilized making a dispersion with a final solids concentration of 2% and a final pH of 8 (pH adjusted with potassium hydroxide). To the collagen dispersion is added polyethylene glycol and hydroxyethyl celluose to achieve a final polyethylene glycol and hydroxyethyl celluose concentration of 0.005% and 0.1% respectively. The dispersion is then cast into concave semi spherically shaped polycarbonate molds. The cast dispersion is dried in a two step process in a humidity/temperature controlled chamber. The first step involves a 5 hour step at 18.5 C and 65% RH, and the second step involves a cycle at 25 C and 93% RH until the shields are dry. The dried collagen shield is then exposed to UV light to obtain the desired extent of crosslinking. The crosslinked product is clear, piable, and has a semi-spherical shape which conforms to the curvature of the eye.

What is claimed is:

1. A method for fabricating a transparent shaped article for ophthalmological use from aqueous collagen-containing materials whereby said article is made with minimal residual stress induced deformation from a predetermined shape defined by a mold upon which said article is formed by casting; comprising the steps of casting said aqueous collagen-containing materials upon said mold; preconditioning said materials by partially drying for a period sufficient to set said shape upon said mold at a temperature less than the temperature at which said collagen is denaturized and at a first relative humidity lower than about 80%; continuing the drying in a second relative humidity higher than said first relative humidity and in the range of about 80-99% at a temperature less than the temperature at which collagen is denaturized for a period of time sufficient to provide said shaped article in solid form with minimal residual stress induced deformation.

2. A method according to claim 1 further comprising the step of completely drying said shaped article at a temperature in the range of about 22°-27° C. at a relative humidity in the range of about 80-99%.

3. A method according to claim 1 comprising the steps of
   casting said aqueous collagen-containing materials upon said mold; partially drying said materials for a period of up to about four hours within the temperature range of 17° to 19° C. at a relative humidity within the range of 50% to 65%;
   continuing the drying for an additional period of up to three hours within the temperature range of 17° to 19° C. at a relative humidity within the range of 85% to 95%.

4. A method according to claim 3 comprising the step of completely drying said article within the temperature range of 22° to 27° C. at a relative humidity within the range of 90% to 95%.

5. A method according to claim 1, 2, 3 or 4 wherein the surface of said mold is made of a thermoplastic material.

6. A method according to claim 5 wherein said thermoplastic material is selected from the group consisting of polycarbonate, polyalkylene, and polyurethane.

7. A method according to claim 6 wherein said thermoplastic material comprises polycarbonate.

8. A method according to claim 6 wherein said thermoplastic material comprises polypropylene.

9. A method according to claim 5 wherein the surface wetting properties of said surface are selected to control the thickness of said materials cast upon said mold.

10. A method according to claim 1, 2, 3 or 4 wherein said collagen-containing materials further comprise a surfactant.

11. A method according to claim 10 wherein said surfactant is selected from the group consisting of hydroxyethyl cellulose, polyethylene glycol, polyvinylpyrrolidone, glycerin, polyvinyl alcohol, polyethylene polypropylene glycols and polysorbates.

12. A method according to claim 11 wherein said surfactant comprises hydroxyethyl cellulose.

13. A method according to claim 11 wherein said surfactant comprises polyethylene polypropylene glycols.

14. A method according to claim 10 wherein said surfactant and the amount thereof in said collagen-containing materials are selected to control the thickness of said materials cast upon said mold.

15. A method according to claim 1, 2, 3 or 4 wherein said article is an ophthalmic lenticular device.

16. A method according to claim 15 wherein said device is formed from bovine corium-derived collagen.

17. A method according to claim 15 wherein said article is formed from bovine tendon-derived collagen.

18. A method according to claim 1, 2, 3 or 4 further comprising the step of crosslinking said shaped article after drying.

19. A method according to claim 18 wherein said crosslinking is by dehydrothermal crosslinking.

20. A method according to claim 18 wherein said crosslinking is by ultraviolet radiation.

* * * * *